United States Patent [19]
Nakashima et al.

[11] Patent Number: 6,133,443
[45] Date of Patent: Oct. 17, 2000

[54] OPTICALLY ACTIVE 1,4-DIHYDROPYRIDINE DERIVATIVES AND PROCESS FOR THE PREPARATION THEREOF

[75] Inventors: Takashi Nakashima, Fujisawa; Kunio Isshiki, Chigasaki; Noriaki Sakata, Yokohama; Naoki Agata, Fujisawa; Takeo Yoshioka, Ayase, all of Japan

[73] Assignee: Mercian Corporation, Tokyo, Japan

[21] Appl. No.: 09/125,608

[22] PCT Filed: Nov. 21, 1996

[86] PCT No.: PCT/JP96/03414

§ 371 Date: Aug. 21, 1998

§ 102(e) Date: Aug. 21, 1998

[87] PCT Pub. No.: WO97/30987

PCT Pub. Date: Aug. 28, 1997

[30] Foreign Application Priority Data

Feb. 23, 1996 [JP] Japan ..................... 8-060359

[51] Int. Cl.[7] ............... C07D 251/00; C07D 401/00; C07D 213/79; C07D 417/00; C07D 403/00
[52] U.S. Cl. ................. 544/180; 544/180; 544/238; 544/333; 544/405; 546/256; 546/263; 546/269.7; 546/275.1
[58] Field of Search ........................ 544/238, 405, 544/180, 333; 546/269.7, 263, 275.1, 256

[56] References Cited

FOREIGN PATENT DOCUMENTS

| 49-133381 | 12/1974 | Japan . |
| 60-48970 | 3/1985 | Japan . |
| 61-194069 | 8/1986 | Japan . |
| 4-321682 | 11/1992 | Japan . |

OTHER PUBLICATIONS

Watanabe et al., "L–Type Ca Channel Block by Highly Hydrophilic Dihydropyridines in Single Ventricular Cells of Guinea–pig Hearts," J. Mol. Cell. Cardiol., vol. 27, No. 6, pp. 1271–1279, 1995.

Boer et al., "Interaction of cytostatics and chemosensitizers with the dexniguldipine binding site on P–glycoprotein," Eur. J. Pharmacol., vol. 295, No. 2/3, pp. 253–260, Jan. 1996.

Boer et al., "Reversible Labeling of a Chemosensitizer Binding Domain of p–Glycoprotein with a Novel 1,4–Dihydropyridine Drug Tansport Inhibitor," Biochemistry, vol. 35, No. 5, pp. 1387–1396, 1996.

*Primary Examiner*—Mukund J. Shah
*Assistant Examiner*—Ben Schroeder
*Attorney, Agent, or Firm*—Louise A. Foutch; Dennis G. LaPointe; Mason & Assoc., P.A.

[57] ABSTRACT

Optically active 1,4-dihydropyridine derivatives represented by general formula (I) and anion salts thereof and a production method therefor:

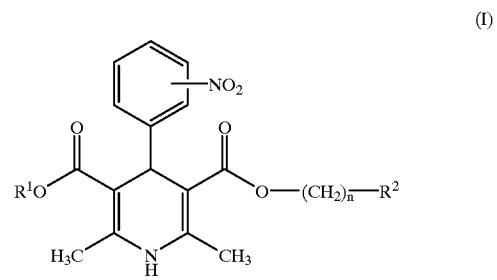

(I)

(wherein $R^1$ represents a $C_{1-6}$ alkyl group, $R^2$ represents a nitrogen-containing heterocyclic group forming a quaternary ammonium which may be substituted, and n is an integer of 1, 2 or 3). The optically active 1,4-dihydropyridine derivatives represented by general formula (I) have vasodilating activity and hypotensive activity and are excellent in water solubility so that they are useful as a drug for circulatory system such as a hypotensor or vasodilator.

10 Claims, No Drawings

OPTICALLY ACTIVE 1,4-DIHYDROPYRIDINE DERIVATIVES AND PROCESS FOR THE PREPARATION THEREOF

TECHNICAL FIELD

The present invention relates to optically active 1,4-dihydropyridine derivatives useful as circulatory system drugs such as hypotensors and vasodilators and to a production method therefor.

BACKGROUND ART 1,4-Dihydropyridine derivatives, such as nifedipine and nirvadipine, have calcium antagonism and, hence, are useful as a circulatory system drug such as a hypotensor and a vasodilator. However, their water solubility is insufficient so that it has been tried to convert them into inclusion compounds with cyclodextrin, i.e., forms with an increased water solubility, in order to impart them with pharmaceutical characteristics such as bioavailability and controlled release (Japanese Patent Application (Kokai) No. 6-100537).

It has also been tried to increase the water solubility of 1,4-dihydropyridine derivatives by introducing a basic tertiary amino group into themselves to form a medically acceptable salt.

For example, (4S)-2,6-dimethyl-4-(3-nitrophenyl)-1,4-dihydropyridine-3,5-dicarboxylic acid (3S)-3-(1-benzyl-3-pyrrolidinyl) ester 5-methyl ester (YM-09730) represented by the following formula

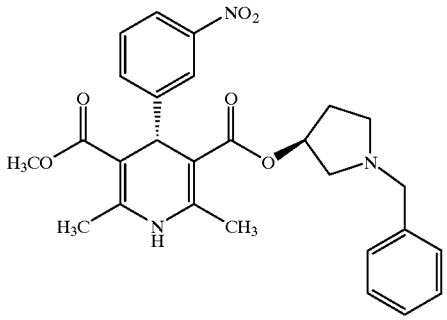

[J. Med. Chem., 29, 2504 (1986)], (4S)-2,6-dimethyl-4-(3-nitrophenyl)-1,4-diydropyridine-3,5-dicarboxylic acid 3-{2-[4-(4-benzhydryl-1-piperazinyl)phenyl]ethyl} ester 5-methyl ester represented by the following formula

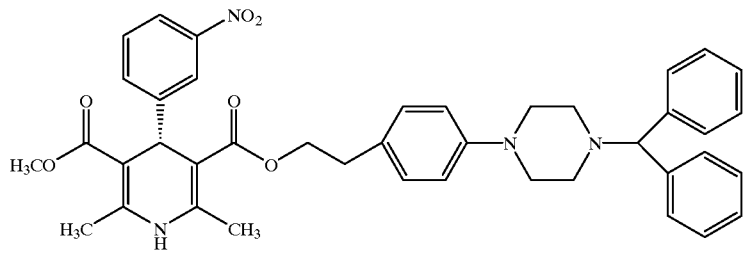

[Chem. Pharm. Bull., 39, 108 (1991)] and salts thereof are known to have calcium antagonistic activity as well as vasodilating activity and hypotensive activity, with these activities lasting [Arzneim. -Forsch./Drug Res. 38(11), 1666 (1988), J. Med. Chem., 29, 2504 (1986), and Japanese Patent Publication (Kokoku) No. 57-30111]

However, only few 1,4-dihydropyridine derivatives have been known that themselves have electric charges and are imparted with, in a sense, permanent water solubility [J. Med. Chem., 3, 3743 (1993)].

Therefore, an object of the present invention is to provide optically active 1,4-dihydropyridine derivatives having themselves electric charges and permanently having water solubility.

Another object of the present invention is to provide a production method for producing such optically active 1,4-dihydropyridine derivatives.

DISCLOSURE OF THE INVENTION

As a result of intensive investigation, the present inventors have found that novel optically active 1,4-dihydropyridine derivatives represented by general formula (I)

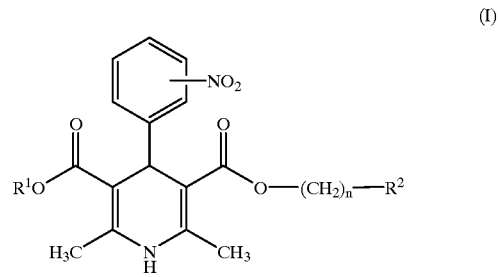

(I)

(wherein $R^1$ represents a $C_{1-6}$ alkyl group, $R^2$ represents a nitrogen-containing heterocyclic group forming a quaternary ammonium salt which may be substituted, and n is an integer of 1, 2 or 3) and anion salts thereof have excellent vasodilating and hypotensive activities and also excellent water solubility, and completed the present invention based on the discovery.

That is, the present invention relates to optically active 1,4-dihydropyridine derivatives represented by general formula (I)

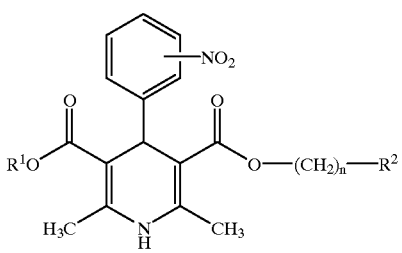

(I)

(wherein the symbols have the same meanings as defined above) and anion salts thereof and to a production method therefor.

Hereafter, the present invention will be described in greater detail.

In general formula (I), the $C_{1-6}$ alkyl group represented by $R^1$ may be a linear, branched or cyclic alkyl group. Its examples include a methyl group, an ethyl group, a propyl group, an isopropyl group, a butyl group, a t-butyl group, and a cyclohexyl group.

In general formula (I), the nitrogen-containing heterocyclic group represented by $R^2$ may include at least one nitrogen atom as a ring-forming atom and form a quaternary ammonium. The heterocyclic ring is preferably an aromatic ring, examples of which include a pyridinium group, a pyridazinium group, a pyrimidinium group, a pyrazinium group, a triazinium group, an imidazolium group, a pyrazolium group, an oxazolium group, and a thiazolium group.

These heterocyclic groups may be substituted. Examples of the substituent include a cyano group, a $C_{1-4}$ alkyl group, a $C_{2-5}$ alkoxycarbonyl group, a dialkylamino group having 1–4 carbon atoms in each alkyl moiety, and a carbamoyl group. Preferred examples of $R^2$ include pyridinium, 4-methylpyridinium, 3-carbamoylpyridinium, 3-cyanopyridinium, 3-methoxycarbonylpyridinium, 4-dimethylaminopyridinium, N-methylpyridinium-2-yl, pyridazinium, 3-methylpyridazinium, 3-cyanopyridazinium, pyrimidinium, 2-methylpyrimidinium, 4-cyanopyrimidinium, 4-carbamoylpyrimidinium, pyrazinium, 2-methylpyrazinium, 2-carbamoylpyrazinium, 2-cyanopyrazinium, triazinium, N-methylimidazolium, N-ethylimidazolium, N-methylpyrazolium, oxazolium, and thiazolium.

[Production Method]

(A) Of the optically active 1,4-dihydropyridine derivatives of the present invention represented by general formula (I) above, those compounds of which the ring-forming nitrogen atom in $R^2$ is connected to a methylene group to form a quaternary ammonium and which are represented by general formula (Ia)

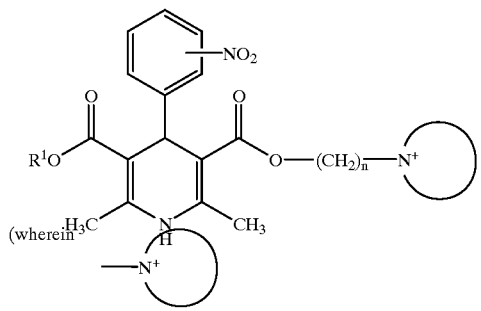

(Ia)

has the same meaning as $R^2$ above, provided that the ring-forming nitrogen atom is connected to a methylene group to form a quaternary ammonium, and $R^1$ and n have the same meanings as defined above) can be produced by condensing an optically active 1,4-dihydropyridine derivative represented by general formula (II) with an alkyl dihalide represented by general formula (III) to obtain an optically active 1,4-dihydropyridine derivative represented by general formula (IV) and reacting this derivative with a nitrogen-containing heterocyclic compound represented by general formula (V) to convert it to a quaternary ammonium as shown in Reaction Scheme A below.

Reaction Scheme A

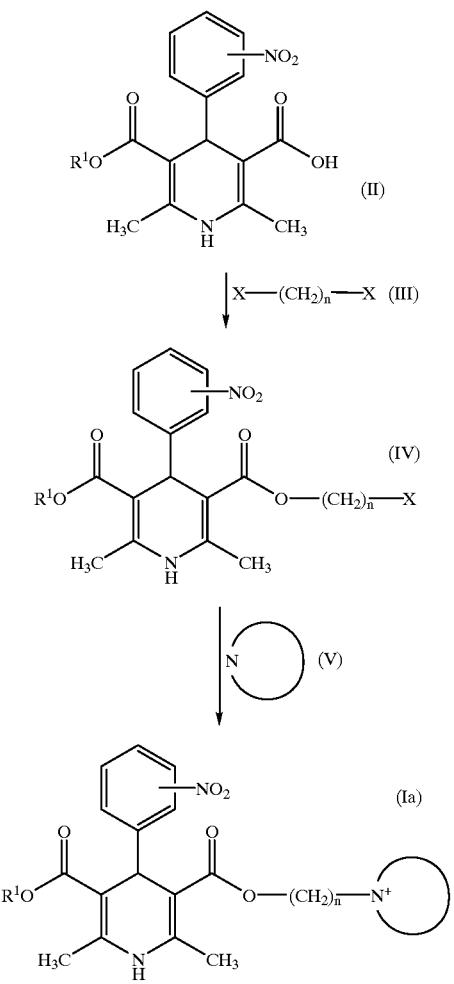

In Reaction Scheme A above, X represents a halogen atom and other symbols have the same meanings as defined above.

The condensation reaction between the compound represented by general formula (II) and the compound represented by general formula (III) can be carried out by a known method. For example, this reaction can be performed by dissolving the compound represented by general formula (II) in a solvent which is inert in itself (for example, tetrahydrofuran, N,N-dimethylformamide, dioxane, chloroform, toluene, or the like) and reacting it with the alkyl dihalide represented by general formula (III) in the presence of an inorganic base (for example, sodium carbonate, potassium carbonate, sodium hydride, or the like) or an organic base (for example, triethylamine, pyridine, lutidine, N-methylmorpholine, or the like).

Here, the optically active intermediates represented by general formula (II) are known and can be produced by the chemical method of Sibanuma et al. [Chem. Pharm. Bull., Vol.28, 2809 (1980)], enzymatic method of Achiwa et al. [Tetrahedron Letters, 32, 5805 (1991)], and enzymatic method of Charles J. Sih et al. [Tetrahedron Letters, 32, 3465 (1991)].

Also, the halogen atom represented by X in general formula (III) includes chlorine, bromine, iodine, etc. Specific examples of the compound represented by general formula (III) include 1,2-dichloroethane, 1,2-dibromoethane, 1,2-diiodoethane, 1,3-dichloropropane, 1,3-dibromopropane, 1,3 -diiodopropane, etc.

The reaction between the resulting optically active form represented by general formula (IV) and the nitrogen-containing heterocyclic compound represented by general formula (V) can also be performed by a known method.

That is, the reaction is carried out by heating the two compounds at 50 to 150° C., preferably 80 to 120° C., after dissolving them in a solvent which is inert in itself, for example, toluene, isopropyl ether, acetonitrile, tetrahydrofuran, N,N-dimethylformamide, dioxane, or the like, or without using any solvent.

Here, the nitrogen-containing heterocyclic compound represented by general formula (V) is a heterocyclic compound having at least one nitrogen atom as a ring-forming atom, preferably an aromatic compound. Specific examples thereof include pyridine, pyridazine, pyrimidine, pyrazine, triazine, imidazole, pyrazole, oxazole, thiazole, etc. These heterocyclic compounds may be substituted. The substituents include a cyano group, a $C_{1-4}$ alkyl group, a $C_{2-5}$ alkoxycarbonyl group, a dialkylamino group having 1 to 4 carbon atoms in each alkyl moiety, a carbamoyl group, etc. Preferred heterocyclic compounds are pyridine, 4-methylpyridine, 3-carbamoylpyridine, 3-cyanopyridine, 3-methoxycarbonylpyridine, 4-dimethylaminopyridine, pyridazine, 3-methylpyridazine, 3-cyanopyridazine, pyrimidine, 2-methylpyrimidine, 4-cyanopyrimidine, 4-carbamoylpyrimidine, pyrazine, 2-methylpyrazine, 2-carbamoylpyrazine, 2-cyanopyrazine, triazine, N-methylimidazole, N-ethylimidazole, N-methylpyrazole, oxazole, thiazole, etc.

(B) Of the optically active 1,4-dihydropyridine derivatives represented by general formula (I) above, those compounds of which $R^2$ is connected to the methylene group through an atom other than the nitrogen atom that forms a quaternary ammonium and which is represented by general formula (Ib)

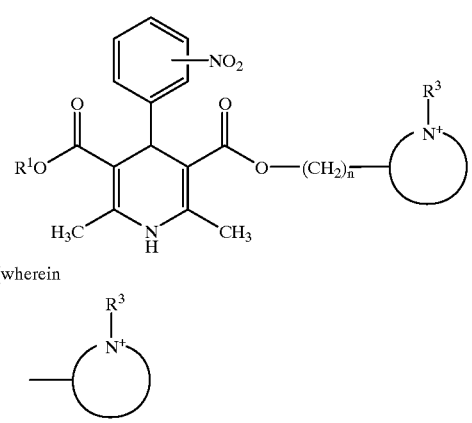

(wherein has the same meaning as $R^2$ above, [provided that the ring-forming atoms include a nitrogen atom which is not connected to the methylene group], $R^3$ represents a $C_{1-6}$ alkyl group, and $R^1$ and n have the same meanings as defined above) can be produced by reacting the optically active 1,4-dihydropyridine derivative represented by general formula (II) with the compound represented by general formula (VI) to obtain an optically active 1,4-dihydropyridine derivative represented by general formula (VII) and alkylating this derivative to convert it to a quaternary ammonium as shown in Reaction Scheme B below.

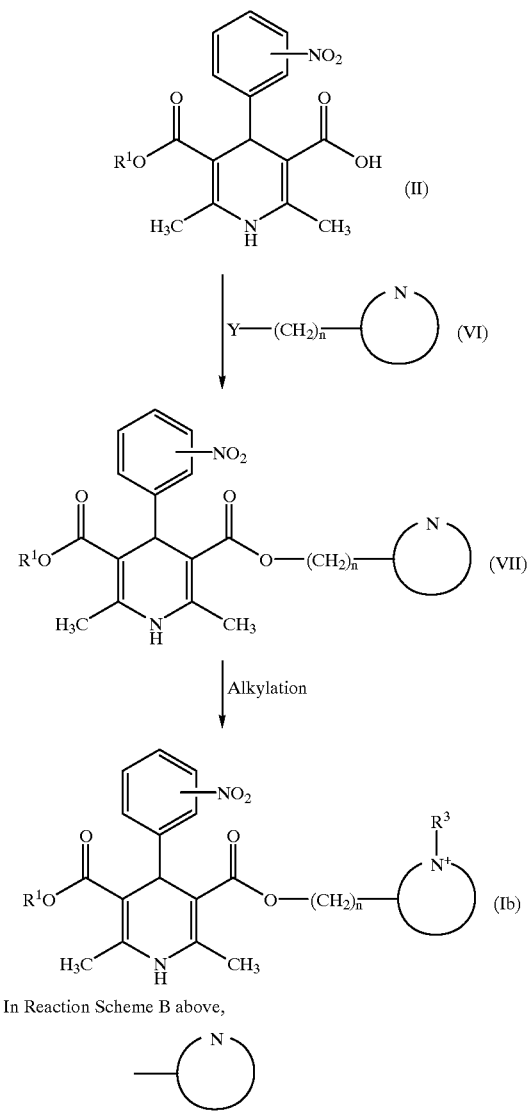

In Reaction Scheme B above, represents a nitrogen-containing heterocyclic group which may be substituted, provided that the ring-forming atoms include a nitrogen atom which is not connected to the methylene group, Y represents a hydroxyl group or a halogen atom, and other symbols have the same meanings as defined above.

The reaction between the compound represented by general formula (II) and the compound represented by general formula (VI) can be carried out by a known method.

For example, the reaction is performed by dissolving the compound represented by general formula (II) in a solvent which is inert in itself (for example, toluene, isopropyl ether, acetonitrile, tetrahydrofuran, N,N-dimethylformamide, dioxane, etc.) in the presence of an inorganic base (for example, sodium hydrogen carbonate, potassium hydrogen carbonate, sodium carbonate, potassium carbonate, etc.) and/or an organic base (for example, triethylamine, pyridine, lutidine, N-methylmorpholine, etc.) or in the presence of a suitable condensing agent, for example, dicyclohexylcarbodiimide or 1-ethyl-3-(3-dimethylaminopropyl)carbodiimide, and reacting it with the compound represented by general formula (VI).

Here, in general formula (VI), the heterocyclic group represented by

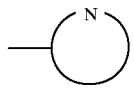

is a heterocyclic group which has at least one nitrogen atom as a nitrogen-forming atom, preferably an aromatic ring. Specific examples include pyridyl, pyridazyl, pyrimidyl, pyrazyl, triazyl, imdazolyl, pyrazolyl, oxazolyl, thiazolyl, etc. These heterocyclic groups may be substituted. The substituents include a cyano group, a $C_{1-4}$ alkyl group, a $C_{2-5}$ alkoxycarbonyl group, a dialkylamino group having 1 to 4 carbon atoms in each alkyl moiety, a carbamoyl group, etc. The halogen atom represented by Y includes chlorine, bromine, iodine, etc.

Specific examples of the compound represented by general formula (VI) include 2-(chloromethyl)pyridine, 2-(bromomethyl)pyridine, 3-(chloromethyl)pyridine, 4-(bromomethyl)pyridine, 2-(hydroxymethyl)pyridine, 3-(hydroxymethyl)pyridine, 2-(2-chloroethyl)pyridine, 2-(2-bromoethyl)pyridine, 3-(2-chloroethyl)pyridine, 4-(2-bromoethyl)pyridine, 2-(2-hydroxyethyl)pyridine, 3-(2-hydroxyethyl)pyridine, etc.

The alkylation of the resulting optically active form represented by general formula (VII) can be carried out by heating the optically active form and a $C_{1-6}$ alkyl halide, for example, methyl iodide, ethyl iodide, or bromoethane at 50 to 150° C., preferably 60 to 120° C., after dissolving them in a solvent which is inert in itself, for example, toluene, isopropyl ether, acetonitrile, tetrahydrofuran, N,N-dimethylformamide, dioxane, or the like, or without using any solvent.

[Anion salt]

The optically active 1,4-dihydropyridine derivatives of the present invention are obtained in the form of anion salts which are derived from raw materials (halogen compounds) used in the production method. That is, the 1,4-dihydropyridine derivatives represented by general formula (Ia) can be obtained as anion salts of the halogen atom X in the alkyl dihalide in general formula (III). Also, the 1,4-dihydropyridine derivatives represented by general formula (Ib) can be obtained as anion salts of the halogen atom in the alkylating agent used in the final step.

In the present invention, the anion salts represented by general formulae (Ia) or (Ib) can be converted to anion salts other than those anion salts which are derived from the above-described raw materials by a conventional method.

Preferred anion salts are hydroxyl ions ($OH^-$), phosphate ions ($PO_4^{3-}$), sulfate ions ($SO_4^{2-}$), carbonate ions ($CO_3^{2-}$), nitrate ions ($NO_3^-$), bromide ions ($Br^-$), chloride ions ($Cl^-$), and fluoride ions ($F^-$).

BEST MODE FOR CARRYING OUT THE INVENTION

Hereafter, the present invention will be described by examples, reference examples and test examples. However, the present invention should not be construed as being limited thereto.

EXAMPLE 1

Production of 3-Iodopropyl (4S)-1,4-dihydro-2,6-dimethyl-5-methoxycarbonyl-4-(3-nitrophenyl)pyridine-3-carboxylate

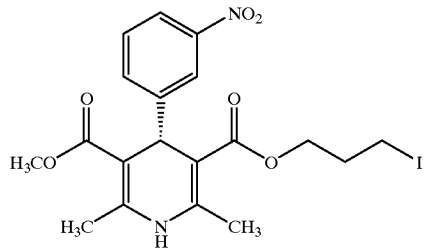

To a solution of 6 g (8.07 mmol) of (4S)-1,4-dihydro-2,6-dimethyl-5-methoxycarbonyl-4-(3-nitrophenyl)pyridine-3-carboxylic acid in 20 ml of N,N-dimethylformamide (DMF) were added 2.75 g (9.88 mmol) of potassium carbonate and 4.2 ml (36.14 mmol) of 1,3-diiodopropane, and the mixture was stirred at room temperature for 4 hours. The reaction mixture was diluted with 500 ml of ethyl acetate and washed with water (300 ml×2). The ethyl acetate layer was dehydrated and dried over salt cake and the solvent was distilled off under reduced pressure. The residue was passed through silica gel column (toluene-ethyl acetate) for purification to obtain 5.93 g of the target compound.

$^1$H-NMR (CDCl$_3$): δ 8.10 (1H, t, J=2.2), 8.02 (1H, ddd, J=7.7 Hz, 2.2 Hz, 1.1 Hz), 7.63 (1H, d, J=7.7 Hz), 7.41 (1H, t, J=7.7 Hz), 5.84 (1H, s), 5.08 (1H, s), 4.14–4.20 (1H, m), 4.05–4.11 (1H, m), 3.66 (3H, s), 2.98–3.08 (2H, m), 2.39 (3H, s), 2.36 (3H, s), 2.05–2.12 (2H, m), FAB-MS(m/z): 501(M+1)

EXAMPLE 2

Production of 3-pyridiniumpropyl (4S)-1,4-dihydro-2,6-dimethyl-5-methoxycarbonyl-4-(3-nitrophenyl)-pyridine-3-carboxylate iodide

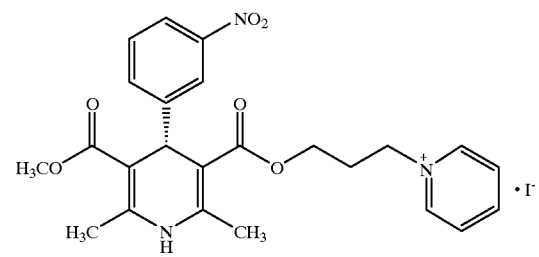

To 657 mg (1.31 mmol) of the 3-iodopropyl (4S)-1,4-dihydro-2,6-dimethyl-5-methoxycarbonyl-4-(3-nitrophenyl)-pyridine-3-carboxylate obtained in Example 1 was added 1.1 ml (13.14 mmol) of pyridine and the mixture was stirred at 80° C. for 4 hours. To the reaction mixture was added 5 ml of chloroform and the resulting mixture was stirred at room temperature for 30 minutes and the crystals formed were filtered to obtain 563 mg of the target compound.

$^1$H-NMR (CD$_3$OD): δ 8.96 (2H, d, J=5.5 HZ), 8.60 (1H, t, J=8.1 Hz), 7.99–8.13 (3H, m), 8.00 (1H, ddd, J=8.1 Hz, 2.2 Hz, 1.1 Hz), 7.63–7.65 (1H, m), 7.48 (1H, t, J=8.1 Hz), 4.97 (1H, s), 4.62–4.70 (2H, m), 4.10–4.24 (2H, m), 3.65 (3H, s), 2.35–2.42 (2H, m), 2.34 (3H, s), 2.33 (3H, s), FAB-MS(m/z): 452(M$^+$)

EXAMPLE 3

Production of 3-pyraziniumpropyl (4S)-1,4-dihydro-2,6-dimethyl-5-methoxycarbonyl-4-(3-nitrophenyl)-pyridine-3-carboxylate iodide

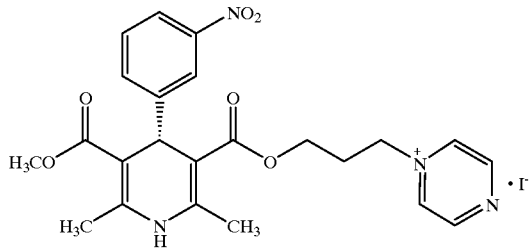

To a solution of 1.46 g (2.92 mmol) of the 3-iodopropyl (4S)-1,4-dihydro-2,6-dimethyl-5-methoxycarbonyl-4-(3-nitrophenyl)-pyridine-3-carboxylate obtained in Example 1 in 2.5 ml of tetrahydrofuran (THF) was added 1.17 g (14.58 mmol) of pyrazine and the mixture was stirred at 100° C. for 3 hours. To the reaction mixture was added 5 ml of ethyl acetate and the mixture was stirred at room temperature for 30 minutes. The crystals formed were filtered to obtain 1.17 g of the target compound.

$^1$H-NMR (CD$_3$OD): δ 9.48 (2H, s), 9.10 (2H, s), 8.08 (1H, s), 8.01 (1H, ddd, J=8.1 Hz, 2.2 Hz, 1.1 Hz), 7.65 (1H, d, J=8.1 Hz), 7.48 (1H, t, J=8.1 Hz), 4.99 (1H, s), 4.71–4.77 (2H, m), 4.15–4.28 (2H, m), 3.65 (3H, s), 2.42–2.45 (2H, m), 2.35 (3H, s), 2.33 (3H, s), FAB-MS(m/z): 453(M$^+$)

EXAMPLE 4

Production of 3-thiazoliumpropyl (4S)-1,4-dihydro-2,6-dimethyl-5-methoxycarbonyl-4-(3-nitrophenyl)-pyridine-3-carboxylate iodide

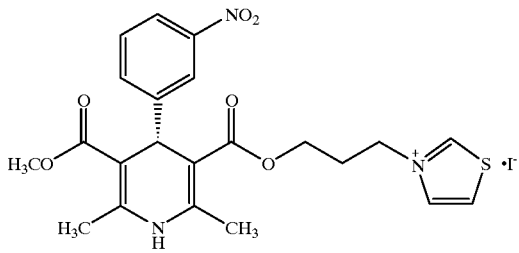

To a solution of 1.00 g (2.00 mmol) of the 3-iodopropyl (4S)-1,4-dihydro-2,6-dimethyl-5-methoxycarbonyl-4-(3-nitrophenyl)-pyridine-3-carboxylate obtained in Example 1 in 2.5 ml of THF was added 710 μl (10.00 mmol) of thiazole and the mixture was stirred at 80° C. for 3 hours. The crystals formed were filtered to obtain 515 mg of the target compound.

$^1$H-NMR (CD$_3$OD): δ 8.46 (1H, d, J=3.7), 8.28 (1H, d, J=4.0), 8.08 (1H, s), 8.00 (1H, dd, J=8.1 Hz, 2.2 Hz), 7.65 (1H, d, J=7.7 Hz), 7.48 (1H, t, J=7.7 Hz), 5.01(1H, s), 4.58–4.63 (2H, m), 4.11–4.20 (2H, m), 3.64 (3H, s), 2.33–2.38 (2H, m), 2.34 (3H, s), 2.33 (3H, s),

FAB-MS(m/z): 458(M$^+$)

EXAMPLE 5

Production of 3-pyridaziniumpropyl (4S)-1,4-dihydro-2,6-dimethyl-5-methoxycarbonyl-4-(3-nitrophenyl)-pyridine-3-carboxylate iodide

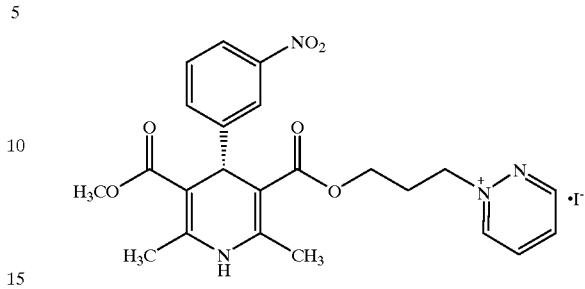

To a solution of 1.00 g (2.00 mmol) of the 3-iodopropyl (4S)-1,4-dihydro-2,6-dimethyl-5-methoxycarbonyl-4-(3-nitrophenyl)-pyridine-3-carboxylate obtained in Example 1 in 2 ml of THF was added 720 μl (10.00 mmol) of pyridazine and the mixture was stirred at 80° C. for 3 hours. A small amount of toluene was added to the reaction mixture, which was subsequently stirred. The crystals formed were filtered. 10 ml of THF was added to the crystals and the mixture was stirred at room temperature for 30 minutes and then filtered to obtain 881 mg of the target compound.

$^1$H-NMR (CD$_3$OD) : δ 9.82 (1H, d, J=5.9 Hz), 9.52 (1H, s), 8.62–8.66(1H, 8.53–8.56 (1H, m), 8.09 (1H, s), 8.01 (1H, ddd, J=7.7 Hz, 2.2 Hz, 1.1 Hz), 8.65 (1H, dd, J=7.7 Hz, 1.1 Hz), 7.48 (1H, t, J=7.7 Hz), 4.99 (1H, s), 4.81–4.84 (2H, m), 4.19–4.22 (2H, m), 3.65 (3H, s), 2.43–2.48 (2H, m), 2.36 (3H, s), 2.35 (3H, s), FAB-MS(m/z): 453(M$^+$)

EXAMPLE 6

Production of 3-(1-methylimidazolium)propyl (4S)-1,4-dihydro-2,6-dimethyl-5-methoxycarbonyl-4-(3-nitrophenyl)-pyridine-3-carboxylate iodide

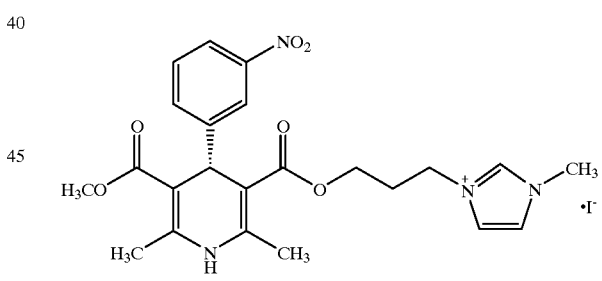

To a solution of 1.00 g (2.00 mmol) of the 3-iodopropyl (4S)-1,4-dihydro-2,6-dimethyl-5-methoxycarbonyl-4-(3-nitrophenyl)-pyridine-3-carboxylate obtained in Example 1 in 2.5 ml of THF was added 820 mg (10.00 mmol) of 1-methylimidazole and the mixture was stirred at 80° C. for 2 hours. To the reaction mixture were added 10 ml of ethyl acetate and 10 ml of toluene, and the mixture was stirred at room temperature for 2 hours. The deposit was passed through silica gel column for purification to obtain 231 mg of the target compound.

$^1$H-NMR (CD$_3$OD): δ 8.08 (1H, s), 8.00 (1H, d, J=8.1 Hz), 7.65 (1H, d, J=8.1 Hz), 7.57–7.58 (2H, m), 7.48 (1H, t, J=8.1 Hz), 5.03 (1H, s), 4.18–4.22 (2H, m), 4.10–4.14 (2H, m), 3.92 (3H, s), 3.64 (3H, s), 2.36 (3H, s), 2.33 (3H, s), 2.18–2.25 (2H, m),

FAB-MS(m/z): 455(M$^+$)

EXAMPLE 7

Production of 3-(3-methoxycarbonylpyridinium)propyl (4S)-1,4-dihydro-2,6-dimethyl-5-methoxycarbonyl-4-(3-nitrophenyl)-pyridine-3-carboxylate iodide

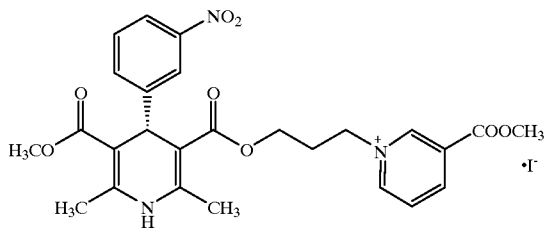

To a solution of 1.00 g (2.00 mmol) of the 3-iodopropyl (4S)-1,4-dihydro-2,6-dimethyl-5-methoxycarbonyl-4-(3-nitrophenyl)-pyridine-3-carboxylate obtained in Example 1 in 2 ml of THF was added 1.37 g (10.00 mmol) of methyl nicotinate and the mixture was stirred at 80° C. for 3.5 hours. The crystals which deposited were filtered to obtain 489 mg of the target compound.

$^1$H-NMR (CD$_3$OD): δ 9.53 (1H, s), 9.20 (1H, d, J=6.2 Hz), 9.03 (1H, dt, J=8.1 Hz, 1.5 Hz), 8.25 (1H, t, J=6.6 Hz), 8.03 (1H, t, J=2.2 Hz), 7.99 (1H, dd, J=7.7 Hz, 1.1 Hz), 7.61 (1H, d, J=7.7 Hz), 7.47(1H,d,J=7.7 Hz), 4.82(1H,s), 4.71–4.80(2H, m), 4.26–4.32 (1H, m), 4.12–4.18 (1H, m), 4.06 (3H, s), 3.65 (3H, s), 2.40–2.47 (2H, m), 2.33 (3H, s), 2.32 (3H, s),

FAB-MS(m/z): 510 (M$^+$)

EXAMPLE 8

Production of 3-(3-cyanopyridinium)propyl (4S)-1,4-dihydro-2,6-dimethyl-5-methoxycarbonyl-4-(3-nitrophenyl)-pyridine-3-carboxylate iodide

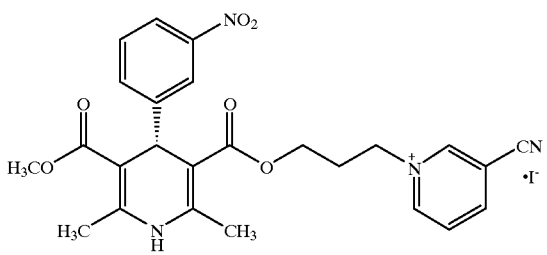

To a solution of 1.00 g (2.00 mmol) of the 3-iodopropyl (4S)-1,4-dihydro-2,6-dimethyl-5-methoxycarbonyl-4-(3-nitrophenyl)-pyridine-3-carboxylate obtained in Example 1 in 2 ml of THF was added 920 mg (10.00 mmol) of nicotinonitrile and the mixture was stirred at 80° C. for 4.25 hours. The crystals which deposited were filtered to obtain 183 mg of the target compound.

$^1$H-NMR (CD$_3$OD) : δ 9.66 (1H, s), 9.27 (1H, d, J=6.6 Hz), 8.98 (1H, dt, J=8.1 Hz, 1.1 Hz), 8.31 (1H, dd, J=8.1 Hz, 6.6 Hz), 8.05 (1H, t, J=2.2 Hz), 8.00 (1H, ddd, J=8.1 Hz, 2.2 Hz, 1.1 Hz), 7.63 (1H, dd, J=7.7 Hz, 1.1 Hz), 7.46 (1H, t, J=8.1 Hz), 4.92 (1H, s), 4.68–4.79 (2H, m), 4.24–4.30 (1H, m), 4.13–4.19 (1H, m), 3.65 (3H, s), 2.40–2.48 (2H, m), 2.35 (3H, s), 2.34 (3H, s), FAB-MS(m/z): 477 (M$^+$)

EXAMPLE 9

Production of 3-(4-dimethylaminopyridinium)propyl (4S)-1,4-dihydro-2,6-dimethyl-5-methoxycarbonyl-4-(3-nitrophenyl)-pyridine-3-carboxylate iodide

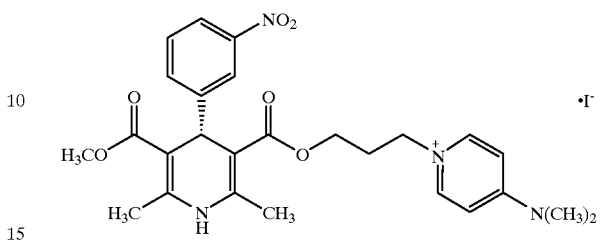

To a solution of 1.00 g (2.00 mmol) of the 3-iodopropyl (4S)-1,4-dihydro-2,6-dimethyl-5-methoxycarbonyl-4-(3-nitrophenyl)-pyridine-3-carboxylate obtained in Example 1 in 4 ml of THF was added 1.22 g (10.00 mmol) of 4-dimethylaminopyridine and the mixture was stirred at 100° C. for 2 hours. The crystals which deposited were filtered to obtain 1.09 g of the target compound.

$^1$H-NMR (CD$_3$OD):δ 8.07 (3H, d, J=8.1 Hz), 8.00 (1H, d, J=8.1 Hz), 7.64 (1H, d, J=7.7 Hz), 7.48 (1H, t, J=8.1 Hz), 6.96 (2H, d, J=7.7 Hz), 4.95 (1H, s), 4.12–4.25 (3H, m), 4.03–4.08 (1H, m), 3.64 (3H, s), 3.23 (6H, s), 2.34 (3H, s), 2.33 (3H, s), 2.18–2.24 (2H, m),

FAB-MS(m/z): 495 (M$^+$)

EXAMPLE 10

Production of 3-(3-carbamoylpyridinium)propyl (4S)-1,4-dihydro-2,6-dimethyl-5-methoxycarbonyl-4-(3-nitrophenyl)-pyridine-3-carboxylate iodide

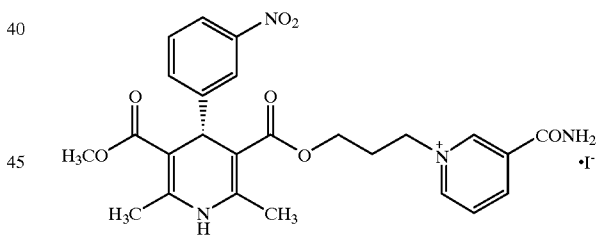

To a solution of 1.00 g (2.00 mmol) of the 3-iodopropyl (4S)-1,4-dihydro-2,6-dimethyl-5-methoxycarbonyl-4-(3-nitrophenyl)-pyridine-3-carboxylate obtained in Example 1 in 4 ml of THF was added 1.22 g (10.00 mmol) of nicotinamide and the mixture was stirred at 80° C. for 3 hours. The crystals which deposited were filtered. To the crystal thus obtained was added 10 ml of THF and the mixture was stirred at room temperature for 30 minutes and filtered to obtain 292 mg of the target compound.

$^1$H-NMR (CD$_3$OD) : δ 9.41 (1H, s), 9.11 (1H, d, J=6.2 Hz), 7.22 (1H, dd, J=8.1 Hz, 6.2 Hz), 8.05 (1H, t, J=1.8 Hz), 7.99 (1H, dt, J=8.1 Hz, 1.1 Hz), 7.63 (1H, d, J=7.7 Hz), 7.47 (1H, t, J=8.1 Hz), 4.90(1H,s), 4.67–4.80(2H,m), 4.24–4.30 (1H,m), 4.13–4.17(1H,m), 3.65(3H,s), 2.42–2.47(2H,m), 2.33(6H, s),

FAB-MS(m/z): 495 (M$^+$)

EXAMPLE 11
Production of 3-(1-methyl-2-pyridinium)methyl (4S)-1,4-dihydro-2,6-dimethyl-5-methoxycarbonyl-4-(3-nitrophenyl)-pyridine-3-carboxylate iodide

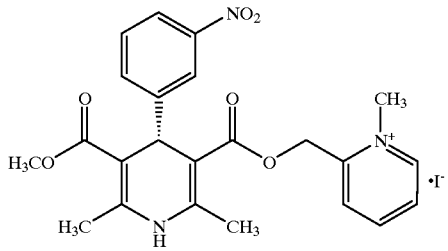

To a solution of 1 g (3.01 mmol) of (4R)-1,4-dihydro-2,6-dimethyl-5-methoxycarbonyl-4-(3-nitrophenyl)-pyridine-3-carboxylic acid in 4 ml of THF were added 1.23 g (7.50 mmol) of 2-(chloromethyl)pyridine and 460 mg (3.35 mmol) of potassium carbonate and the mixture was stirred at room temperature for 5 hours. The mixture was diluted with 50 ml of ethyl acetate, washed with water, and hydrated and dried over salt cake. Thereafter, the solvent was distilled off under reduced pressure to obtain 1.13 g of the residue. The residue was passed through a silica gel column for purification to obtain 673 mg of 3-(2-pyridyl)methyl (4S)-1,4-dihydro-2,6-dimethyl-5-methoxycarbonyl-4-(3-nitrophenyl)-pyridine-3-carboxylate. To a solution of 673 mg of the compound thus obtained in 1 ml of THF was added 1 ml of methyl iodide and the mixture was stirred at 60° C. for 2 hours. The crystals which deposited were filtered to obtain 526 mg of the target compound.

$^1$H-NMR (CD$_3$OD): δ 8.89 (1H, d, J=6.2 Hz), 8.46 (1H, t, J=7.7 Hz), 7.96–8.04 (3H, m), 7.80 (1H, d, J=8.1 Hz), 7.67 (1H, d, J=8.1 Hz), 7.63 (1H, d, J=7.7 Hz), 7.48 (1H, t, J=7.7 Hz), 5.13 (1H, s), 4.80–4.84 (2H, m), 4.25 (3H, s), 4.13–4.17 (1H, m), 3.63 (3H, s), 2.40 (3H, s), 2.33 (6H, s),

FAB-MS(m/z): 438 (M$^+$)

EXAMPLE 12
Production of 3-(1-methyl-3-pyridinium)propyl (4S)-1,4-dihydro-2,6-dimethyl-5-methoxycarbonyl-4-(3-nitrophenyl)-pyridine-3-carboxylate iodide

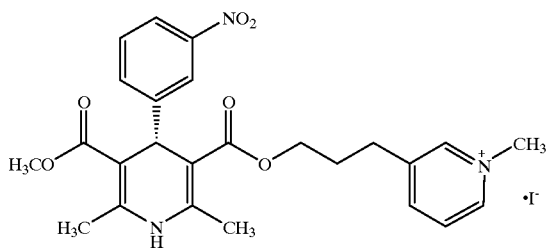

To a solution of 500 mg (1.51 mmol) of (4S)-1,4-dihydro-2,6-dimethyl-5-methoxycarbonyl-4-(3-nitrophenyl)-pyridine-3-carboxylic acid in 3 ml of THF were added 300 ml (2.25 mmol) of 3-pyridinepropanol and 475 mg (3.00 mmol) of 1-ethyl-3-(3'-dimethylaminopropyl) carbodiimide and the mixture was stirred at 80° C. for 4 hours. After concentration, the reaction mixture was diluted with 50 ml of ethyl acetate, washed with water, and hydrated and dried over salt cake. Thereafter, the solvent was distilled off under reduced pressure to obtain 680 mg of the residue. The residue was passed through a silica gel column for purification to obtain 241 mg of 3-(3-pyridyl)propyl (4S)-1,4-dihydro-2,6-dimethyl-5-methoxycarbonyl-4-(3-nitrophenyl)-pyridine-3-carboxylate. To a solution of 241 mg of the compound thus obtained in 1 ml of THF was added 330 μl of methyl iodide and the mixture was stirred at 60° C. for 1 hour. The crystals which deposited were filtered to obtain 229 mg of the target compound.

$^1$H-NMR (CD$_3$OD): δ 8.89 (1H, d, J=6.2 Hz), 7.96–8.44 (3H, m), 7.80 (1H, d, J=8.1 Hz), 6.67 (1H, d, J=8.1 Hz), 7.48 (1H, t, J=7.7 Hz), 5.13 (1H, s), 4.83 (2H, s), 4.25 (3H, s), 3.63 (3H, s), 2.40 (3H, s), 2.32 (3H, s),

FAB-MS(m/z): 438 (M$^+$)

TEST EXAMPLE 1

Test for solubility in water

The solubility in water of the compounds obtained in Examples 2 to 12 were measured. The measurements were performed by mixing deionized water with a compound to be tested, subsequently stirring for 3 minutes using a electromagnetic vibrating stirrer, and determining a critical value (solubility) based on presence or absence of insoluble matter.

As a control compound, the solubility of nifedipine was measured in the same manner.

As a result, the solubility of nifedipine was 0.1 mg/ml or less whereas the compounds of Examples 2 to 12 showed respective solubilities of not lower than 1.0 mg/ml.

TEST EXAMPLE 2

The pharmacological activity of the optically active 1,4-dihydropyridine derivatives of the present invention was confirmed by experiments of dilation against high potassium contraction of rat thoracic aorta.

Thoracic aorta was extracted from a Wistar rat (male, aged 9–12 weeks) and after removing the connective tissue, adipose tissue and the like, there was prepared a spiral specimen of 2 mm wide and 15 mm long. The blood vessel specimen thus obtained was suspended at 37° C. under a load of 1 g in an extracted organ incubator containing 10 ml of a nutrient solution (NaCl: 137 mM, KCl: 5.4 mM, CaCl$_2$: 1.5 mM, MgCl$_2$: 1 mM, NaHCO$_3$: 23.8 mM, glucose: 5.5 mM, pH 7.4) aerated with a mixed gas consisting of 95% oxygen and 5% carbon dioxide, and equilibrated for about 1 hour. The nutrient solution in the extracted organ incubator was exchanged with high concentration potassium ion nutrient solution (NaCl: 77 mM, KCl: 65.4 mM, CaCl$_2$: 1.5 mM, MgCl$_2$: 1 mM, NaHCO$_3$: 23.8 mM, glucose: 5.5 mM, pH 7.4) to cause contraction of the blood vessel specimen. After the contraction reached a stationary stage, test substances (the compounds of Examples 3, 4, 6, 7, 8, and 10 and nifedipine) were added in the incubator and their contraction inhibiting effects were evaluated.

The results obtained are shown in Table below.

TABLE 1

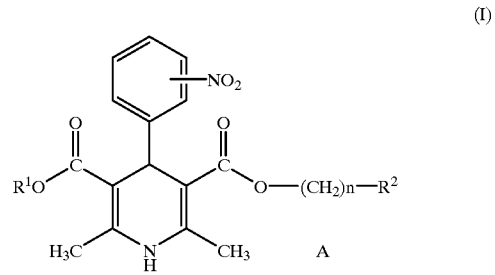

| compound | R | IC$_{50}$ (p mol/l) |
|---|---|---|
| Example 3 | 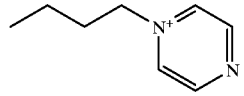 | 2.2 |
| Example 4 | 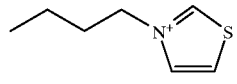 | 3.7 |
| Example 6 | 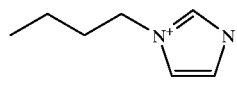 | 1.8 |
| Example 7 | 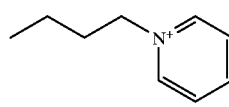 | 3.3 |
| Example 8 | 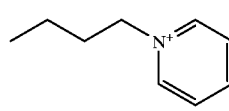 | 2.0 |
| Example 10 | 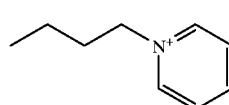 | 2.7 |
| Control | —CH$_3$ (nifedipine) | 3 |

From the table, it can be seen that the optically active 1,4-dihydropyridine derivatives of the present invention had blood vessel dilating effects as potent as nifedipine.

INDUSTRIAL APPLICABILITY

The present invention provides optically active 1,4-dihydropyridine derivatives and their anion salts and method of producing them.

The optically active 1,4-dihydropyridine derivatives of the present invention have excellent blood vessel dilating effects and hypotensive effects and excellent water-solubilities so that they are useful as a drug for circulatory system such as a hypotensor or vasodilator.

What is claimed is:

1. An optically active 1,4-dihydropyridine compound of formula (I)

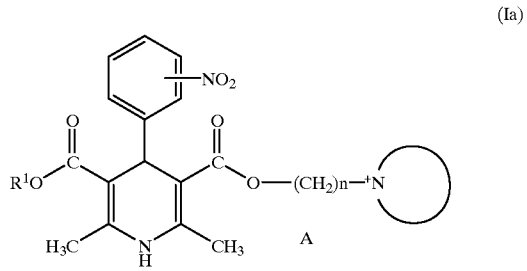

wherein $R^1$ is a $C_1$–$C_6$ alkyl; $R^2$ is a heterocycle of 5 or 6 ring atoms, the heterocycle comprising as ring atoms, in any combination, C, N, S or O and wherein the heterocycle is optionally substituted with $C_1$–$C_4$ alkyl, $C_2$–$C_5$ alkoxycarbonyl, dialkylamino, carbamoyl, or cyano, provided that at least one of the ring atoms is a quaternary ammonium; n is 1, 2 or 3; A is an anion.

2. The optically active 1,4-dihydropyridine compound of claim 1 wherein $R^2$ is pyridinium, pyridazinium, pyrimidinium, pyrazinium, triazinium, imidazolium, pyrazolium, oxazolium, or thiazolium.

3. An optically active 1,4-dihydropyridine compound of formula (Ia):

(Ia)

[structure]

wherein $R^1$ is $C_1$–$C_6$ alkyl;

is a heterocycle of 5 or 6 ring atoms, the heterocycle comprising as ring atoms, in any combination, C, N, S or O, and wherein the heterocycle is optionally substituted with $C_1$–$C_4$ alkyl, $C_2$–$C_5$ alkoxycarbonyl, dialkylamino, carbamoyl or cyano; n is 1, 2 or 3; A is an anion.

4. The optically active 1,4-dihydropyridine compound of claim 3 wherein

is pyridinium, pyridazinium, pyrimidinium, pyrazinium, triazinium, imidazolium, pyrazolium, oxazolium or thiazolium.

5. An optically active 1,4-dihydropyridine compound of formula (Ib);

(Ib)

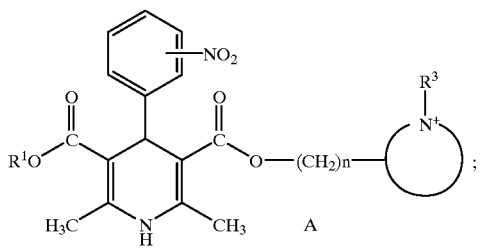

wherein $R^1$ is $C_1$–$C_6$ alkyl;

is a heterocycle of 5 or 6 ring atoms, the heterocycle comprising as ring atoms, in any combination, C, N, S, or O, and wherein the heterocycle is optionally substituted with $C_1$–$C_4$ alkyl, $C_2$–$C_5$ alkoxycarbonyl, dialkylamino, carbamoyl, or cyano, provided that the ring-forming atoms include a nitrogen atom which is not connected to the methylene group; $R^3$ is $C_1$–$C_6$ alkyl; n is 1, 2 or 3; A is an anion.

6. The optically active 4-dihydropyridine compound of claim 5 wherein is pyridinium, pyridazinium, pyrimidinium, pyrazinium, trianzinium, imidazolium, pyrazolium, oxazolium, or thiazolium.

7. A method for preparing an optically active 1,4-dihydropyridine compound of formula (Ia):

(Ia)

wherein $R^1$ is $C_1$–$C_6$ alkyl;

is a heterocycle of 5 or 6 ring atoms, the heterocycle comprising as ring atoms, in any combination, C, N, S, or O and wherein the heterocycle is optionally substituted with $C_1$–$C_4$ alkyl, $C_2$–$C_5$ alkoxycarbonyl, dialkylamino, carbamoyl or cyano; n is 1, 2 or 3; A is an anion, comprising the steps of:

a) reacting an optionally active 1,4-dihydropyridine compound of formula (II)

(II)

wherein $R^1$ is $C_1$–$C_6$ alkyl, with a compound of formula (III)

$$X-(CH_2)_n-X,$$ (III)

wherein X is halogen and n is 1, 2 or 3, to form a compound of formula (IV)

(IV)

b) reacting the compound produced in step a) having formula (IV) with a heterocycle represented by formula (V)

(V)

wherein comprises 5 or 6 ring atoms, the heterocycle comprising as ring atoms, in any combination, C, N, S, or O, and wherein the heterocycle is optionally substituted with $C_1$–$C_4$ alkyl, $C_2$–$C_5$ alkoxycarbonyl, dialkylamino, carbamoyl, or cyano, thereby producing the compound of formula (Ia).

8. The method of claim 7 wherein is pyridinium, pyridazinium, pyrimidinium, pyrazinium, triazinium, imidazolium, pyrazolium, oxazolium or thiazolium.

9. A method for preparing an optically active 1,4-dihydropyridine compound of formula (Ib)

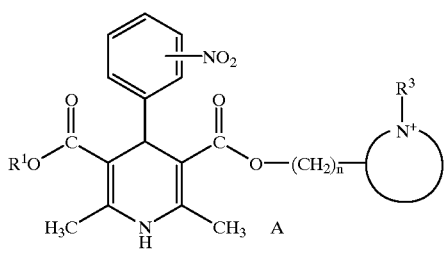
(Ib)

wherein $R^1$ is $C_1$–$C_6$ alkyl;

is a heterocycle of 5 or 6 ring atoms, the heterocycle comprising as ring atoms, in any combination, C, N, S or O and wherein the heterocycle is optionally substituted with $C_1$–$C_4$ alkyl, $C_2$–$C_5$ alkoxycarbonyl, dialkylamino, carbamoyl or cyano, provided that if the heterocycle ring atom bonded to methylene is N it does not form a quaternary ammonium; $R^3$ is $C_1$–$C_6$ alkyl; n is 1, 2 or 3; A is an anion, comprising the steps of:

a) reacting an optically active 1,4-dihydropyridine compound of formula (II)

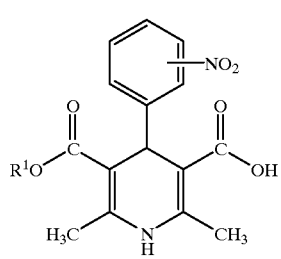
(II)

wherein $R^1$ is $C_1$–$C_6$ alkyl, with a compound of formula (VI)

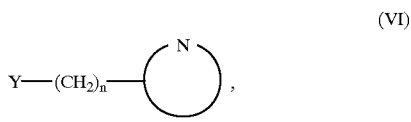
(VI)

wherein Y is halogen or hydroxyl and n is 1,2 or 3, thereby forming a compound of formula (VII)

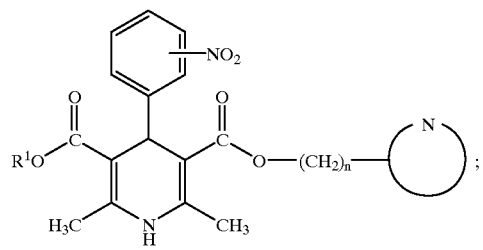
(VII)

b) reacting the compound of formula (VII) formed in step a) with a compound represented by X—$R^3$, wherein $R^3$ is C1–C6 alkyl and X is halogen, thereby forming the compound of formula (Ib).

10. The method of claim 9 wherein

is pyridinium, pyridazinium, pyrimidinium, pyrazinium, triazinium, imidazolium, pyrazolium, oxazolium or thiasolium.

* * * * *

UNITED STATES PATENT AND TRADEMARK OFFICE
CERTIFICATE OF CORRECTION

PATENT NO : 6,133,443
DATED : October 17, 2000
INVENTOR(S) : Nakashima et al.

It is certified that error appears in the above-identified patent and that said Letters Patent are hereby corrected as shown below:

On title page, item 75 Inventors replace "Takashi Nakashima, Fujisawa; Kunio Isshiki, Chigasaki; Noriaki Sakata, Yokohama; Noaki Agata, Fujisawa; Takeo Yoshioka, Ayase, all of Japan"

with -- Takashi Nakashima; Kunio Isshiki; Noriaki Sakata; Naoki Agata; Takeo Yoshioka, all of Kanagawa, Japan --

Signed and Sealed this

Eighth Day of May, 2001

*Attest:*

NICHOLAS P. GODICI

*Attesting Officer*   Acting Director of the United States Patent and Trademark Office